United States Patent
Wolter

(10) Patent No.: US 6,322,562 B1
(45) Date of Patent: Nov. 27, 2001

(54) FIXATION SYSTEM FOR BONES

(76) Inventor: Dietmar Wolter, c/o Berufsgenossenschaftliches Unfallkrankenhaus Bergedorfer Strass 10, D-21033 Hamburg (DE)

(*) Notice: Subject to any disclaimer, the term of this patent is extended or adjusted under 35 U.S.C. 154(b) by 0 days.

(21) Appl. No.: 09/464,304

(22) Filed: Dec. 15, 1999

(30) Foreign Application Priority Data

Dec. 19, 1998 (DE) .............................. 198 58 889

(51) Int. Cl.[7] .................................. A61B 17/80
(52) U.S. Cl. ..................... 606/69; 606/60; 606/73
(58) Field of Search ................. 606/60, 62, 64, 606/69, 72, 73, 74

(56) References Cited

U.S. PATENT DOCUMENTS

| | | | |
|---|---|---|---|
| 3,744,488 | * | 7/1973 | Cox . |
| 4,493,317 | * | 1/1985 | Klaue ..................... 606/69 |
| 5,534,032 | | 7/1996 | Hodorek ................. 623/18 |
| 5,601,553 | * | 2/1997 | Trebling et al. ........ 606/73 X |
| 5,607,428 | * | 3/1997 | Lin ........................... 606/69 |
| 5,709,686 | * | 1/1998 | Talos et al. ............. 606/69 |
| 5,810,823 | | 9/1998 | Klaue et al. ............ 606/69 |
| 5,961,524 | * | 10/1999 | Crombie ................ 606/104 |
| 6,030,162 | * | 2/2000 | Huebner ............. 606/73 X |

FOREIGN PATENT DOCUMENTS

| | | |
|---|---|---|
| 196 29 011 A1 | 1/1998 | (DE) . |
| 43 43 117 C2 | 11/1999 | (DE) . |
| 0 201 024 | 1/1986 | (EP) . |
| 97/09000 A | 3/1997 | (WO) . |
| 89/04150 | 5/1999 | (WO) . |

* cited by examiner

*Primary Examiner*—Jeffrey A. Smith
(74) *Attorney, Agent, or Firm*—Vidas, Arrett & Steinkraus P.A.

(57) ABSTRACT

A fixation system for bones including a connection carrier with at least one passage hole and at least one bone screw inserted into the at least one passage hole. The connection carrier including a seat surface and the bone screw including a seat surface, permitting a mutual alignment at various angles for fixing the bone screw at a certain angle to the connection carrier. The bone screw further including a preformed thread below the bone screw seat surface, the preformed thread deforming a portion of the passage hole below the seat surface of the connection carrier when the bone screw is screwed in so that a thread connection is formed between the bone screw thread and the connection carrier, the deformation being formed by rotating the bone screw at a certain angle to the connection carrier.

36 Claims, 4 Drawing Sheets

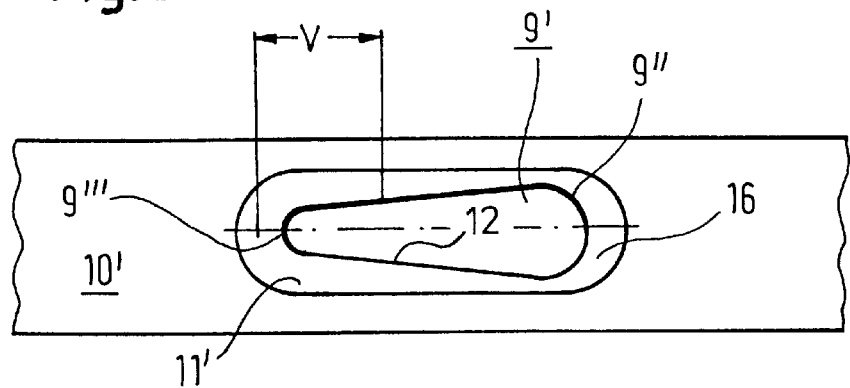
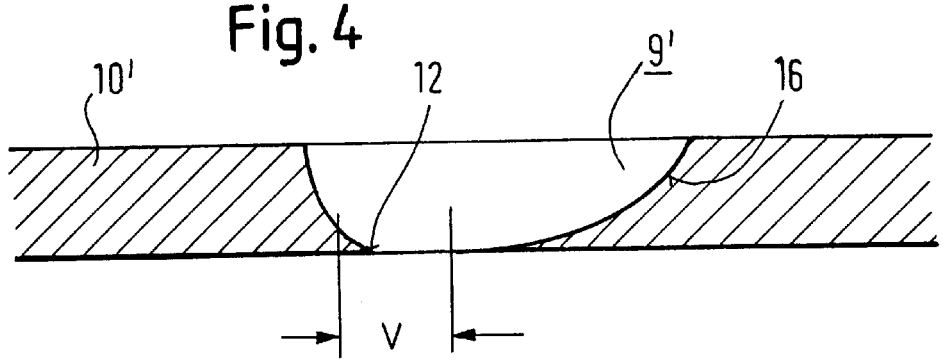
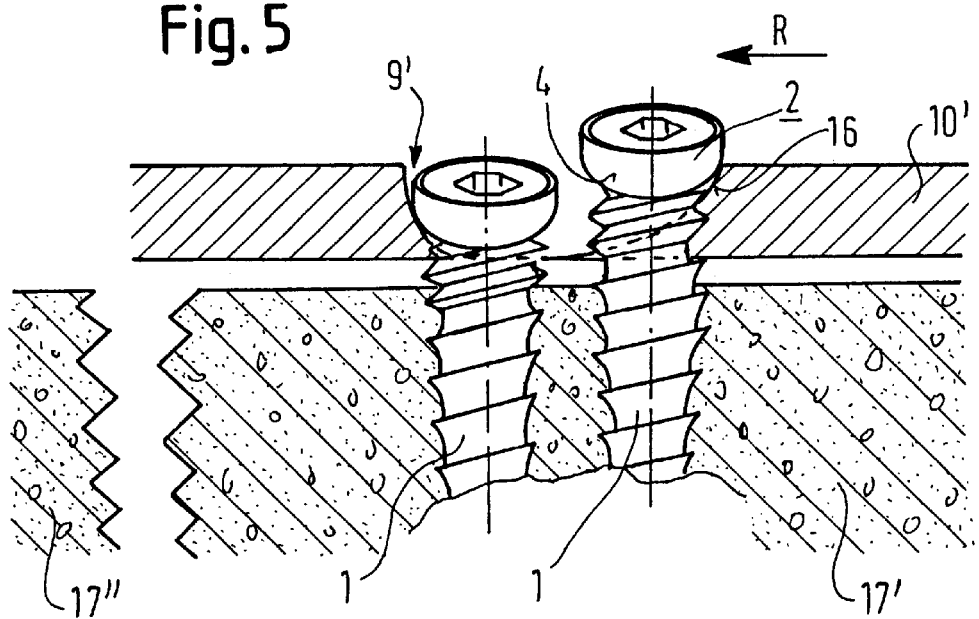

FIXATION SYSTEM FOR BONES

CROSS-REFERENCE TO RELATED APPLICATIONS

None.

STATEMENT REGARDING FEDERALLY SPONSORED RESEARCH

Not Applicable.

BACKGROUND OF THE INVENTION

The invention relates to a fixation system for bones with a connection carrier and at least one bone screw or at least one locking bolt.

Such fixation systems are used in osteosynthesis, wherein the bone screws are connected to the ends of the bone and the connection carrier bridges the fracture. The connection carrier may in particular be a bone plate, a marrowbone nail or a fixator. With this it is desirable, whilst adapting to the nature of the bone part to be connected, for the optical alignment onto the fragments or for compensating target errors, to be able to incorporate the bone screws at different angles into the connection carrier.

For this with a known fixation system the bone screws have heads with a roughly hemispherical-shaped seat surface of which one seat surface in passage holes is allocated to a bone plate. If for example with a tibia fracture the two bone pieces must be connected to one another, the metallic bone plate is applied onto the set-up bone pieces. Thereafter the screws are rotated into the bones such that the seat surfaces of the screw heads and of the plate holes come to bear on one another and the plate is pressed against the bone. From this there results a connection of bone parts, bone plate and bone screws. It however has been shown that a loosening of the connection of bone screws and bone plates may take place. A cause lies in the insufficient stability of the angle connections of bone screw and bone plate which are secured by friction forces between the screw head and the plate hole.

An angular stable connection of the bone screw and bone plate on the other hand leads to a gain in stability of the whole assembly. Various solutions are known in order to achieve such a stable combination. According to EP-A-10 201 024 this may for example be effected in that to the bone plate there is allocated a pressure plate which can be tensioned with the screw heads and fixed to this in a selected angular position. Such complicated fixation systems with a pressure plate are on account of their relatively large volume restricted in their usability.

Another solution according to WO/89 041 50 exists in widening the screw head in a slot region with a spreading screw and by way of this to press it into the plate hole. With this the screw head or the insert surrounding this as well as the plate hole have spherical seat surfaces which permit an alignment at various angles. This fixation system is likewise complicated in the manufacture and application.

Furthermore it is also known to provide the screw head with an outer thread and the plate hole with an inner thread. If then the screw is rotated into the bone then by way of a thread connection there is effected an angularly stable alignment of the plate and screw. This solution has however the grave disadvantage that the screw may not be mounted into the plate hole at any angle but only in the alignment predetermined by the thread axes.

This disadvantage according to DE 43 43 117 A1 is overcome in a manner that the means for fastening the bone screw at a certain angle to the bone plate comprise a threaded connection of the seat surfaces of the bone plate and the bone screw, this thread being formed by rotating in the bone screw at a certain angle by a preformed thread on at least one seat surface. With this the seat surface of the bone screw as well as also the seat surface of the bone plate may comprise a preformed thread. On rotating in the bone screw by way of the at least one thread there arises a deformation of the material in the seat surfaces and thus a formation of a thread connection in the respective screwing direction.

This solution has however in particular with the use of thicker plates the considerable disadvantage that the force for deforming the material is considerable and this intraoperationally may not always be mustered without any problem. In order to make this possible therefore in DE 196 29 011 A1 there is specified an additional bolt-shaped performer for aligning in bone bores with an outer thread for deforming a thread in the passage hole of a connection carrier. This deforming of a thread however has the disadvantage that it requires an additional working procedure and leads to the occurrence of wear and swarf particles from the wall region of the passage hole. Examinations have shown that with the application of pure titanium in the passage hole of a tibia plate there occurs a swarf formation of 0.0001 g per passage hole. A similar quantity also results from conventional metal plates. This is to be seen as disadvantageous for reasons of compatibility as well as due to the fact that here it is case of a foreign body.

BRIEF SUMMARY OF THE INVENTION

Proceeding from this it is the object of the invention to provide a fixation system for bones in which the rotating of the bone screws at various angular positions into the connection carrier is simplified, that however a stable fixation of the bone screw in its angular position to the connection carrier is achieved, wherein the wear and swarf occurrence on forming the thread connection is considerably reduced.

The object is achieved by the inventive fixation systems.

With the inventive fixation system the means for fixing the at least one bone screw comprises a thread connection below the seat surfaces of the bone screw and connection carrier, which is formed by rotating in the bone screw at a certain angle by a preformed thread below at least one of the seat surfaces of the bone screw and connection carrier by way of deformation. By way of the fact that the thread connection is formed by deformation not in the seat surfaces but below these with the participation of at least one preformed thread, the regions of the connection affected by the deformation can be considerably reduced. As a result of this the rotating in of the bone screw is simplified and the intermediate step of the thread forming by way of a special thread former becomes superfluous. Furthermore the production of wear particles and swarf material is reduced to an insignificant level. In spite of this by way of the seat surfaces and the thread connection an angularly stable screw connection with the desired strength is achieved. This may be secured by way of a force fit (friction fit) resulting by way of the deformation and/or a material fit (friction weld) in the thread connection.

The preformed thread may be located below both seat surfaces or below only one of the seat surfaces so that the thread connection whilst deforming at least one preformed thread or a thread-free region is formed below a seat surface. Preferably the thread connection is formed by a preformed thread below the one seat surface and at least one at least partly circumferential projection below the other seat surface, this projection being easily deformable by rotating in the preformed thread. With this the projection may have a design which simplifies its deformation by way of the preformed thread, for example may be shaped fin-like or lip-like. The projection may also—in contrast to a helical-shaped thread—be arranged symmetrically on a circular line about the hole axis, by which means the space requirement for the projection is reduced and the dependence of the rotating-in force on the position of the screwing-in axis to the hole axis is reduced.

Preferably the seat surfaces are spherical or conical, by which means the screwing-in and placing of the bone screws at various angles in the connection carrier is favored. Also preferably the one seat surface is formed on the lower side of the screw head of the bone screw. With this the thread connection may be formed with a section of the screw head below the one seat surface. In this manner the seat surface and means for fixing is formed in a space-saving manner on the bone screw.

According to a further preferred formation the other seat surface is formed in the passage hole of the connection carrier. With this the thread connection may be formed with a connection of the passage hole below the other seat surface. Preferably this section comprises the at least one deformable projection below the other seat surface. With this other seat surfaces and means for fixing also in the connection carrier are accommodated in a space-saving manner. With the previously mentioned formations of the bone screw and connection carrier, bone plates which for example have a thickness of a few millimeters may be formed without the screw head projecting beyond the upper side of the bone plate.

According to a further formation at a distance to the deformable projection there is arranged at least one further, at least partly circumferential projection below the other seat surface, this projection being deformable by rotating in the preformed thread. Then the bone screw after the rotating in is securely seated in several deformable projections, by which means the angular connection may be further stabilized. For the purpose of a further stabilization of the angular connection also above the other seat surface in the passage hole there may be arranged at least yet one further at least partly circumferential projection deformable by rotating in the bone screw. By way of this a—in cross section—swallowtail-shaped shaping of the wall of the passage hole may be given which results in a more favorable screw head and hole wall contact, by which means the stabilization by way of the bone screw, in its angular position, is further stabilized.

With relatively thin connection carriers, e.g. bone plates as they are preferably applied in the region of the ankle joint, the vertebral column of the neck or the end of the lower arm which is distant to the body, which for example may have a thickness of 1 to 2 mm, the connection carrier around the passage hole may have a material thickening. This material thickening may already be present before the application of the bone screw (or thread deformation) or result on rotating in a bone screw by way of material displacement. Preferably the material thickening is formed on the lower side of the connection carrier. Additionally or instead of this it may however also be formed on the upper side of the connection carrier. A material thickening on the lower side of the connection carrier ensures a point-shaped contact between the connection carrier and the bone so that in the contact-free regions the supply to the vessels of the bone surface and thus the healing process is improved. Furthermore by way of the material thickening the submersing of the screw head into the connection carrier is simplified so that the danger of screw head parts projecting is reduced.

Principally the bone screw comprises a shank with a shank thread for rotating into the bone. The shank thread may be a self-cutting thread so that a thread cutting by way of a particular tool may be done away with. The pitch of the preformed thread may be slightly smaller than that of the shank thread of the bone screw in order apart from the angular stability to achieve a pressing force of the connection carrier against the bone surface. This represents an additional important gain of stability in the whole connection.

Also the bone screw may comprise a drill tip so that a predrilling of a hole in the bone may be done away with. For a simple rotating in the screw head may comprise a tool engagement for example a hexagonal inbus. Furthermore the arrangement of conical furrows on the surface of the bone screw is advantageous since these permit an accommodation of the deformed material and thus simplify the incorporation of the bone screw into the passage hole of the connection carrier.

According to a further formation the passage hole has an elongate shape and the upper edge of the passage hole is inclined from a maximum level at one end to a minimum level at the other end, wherein the width of the passage hole reduces from one end towards the other end so that a bone screw introduced in the region of the one end with the screw head is seated on the inclined edge and with a screwing whilst displacing the connection carrier slides with the head lower side on the inclined upper edge until with a closing in on the lower end the preformed thread forms a thread connection. With this the edge in the region of the other end may form the deformable projection below the seat surface located thereunder. By way of rotating in the bone screw thus a displacement of the connection carrier and an accompanying additional compression of the fragment ends is achieved. It is known that by way of such a compression of two fragments the stability is likewise increased. By way of this procedure also disturbing gaps which must be bridged by the healing of the bone, are primarily avoided.

A further improvement is represented by the somewhat oblique arrangement of the passage holes in the connection carrier on various sides of a fracture to be bridged. This oblique position of the distal and proximal passage holes to one another allows the bone screws on implantation to diverge, i.e. with their screw heads are closer together than with their "feet" (for example a drill tip arranged here). By way of this diverging screw position in relationship to the axis of the connection carrier and the bone there is an increased stability and an improved force transition with a loading via the connection carrier and the bones.

With the connection carrier it is in particular the case of a bone plate, a bonemarrow nail or a fixator.

Preferably the preformed thread consists of a harder material than the region to be deformed by this, in particular as a deformable projection. For this the bone screw or its casing may be of a harder material than the connection carrier or the region thereof to be deformed. By way of this the manufacture of the thread connection is further simplified and its strength is further improved.

The fixation system according to claim 25 has a marrow bone nail comprising at least one passage hole, for bridging bone fragments and at least one locking bolt for screwing into the passage hole and into a bone fragment in order to connect this to the marrowbone nail. Furthermore the passage hole comprises an inner thread for forming a thread into the locking bolt. The locking bolt in contrast has a casing region which simplifies the forming-in of the thread by the inner thread at various angles, which reduces the production of wear and swarf and ensures the fixing in the formed-in thread. This is threadless and—for benefiting the ability to be rotated in at various angles—is conical and has a lesser hardness than the core region of the locking bolt which ensures the transmission of higher forces via the locking bolt. For the further help in forming the thread formation and securement of the thread the casing region of the locking bolt may have a lesser hardness than the marrowbone nail at least in the region of the inner thread. Preferably furthermore the locking bolt on both sides of the conical casing region may carry threads with various outer diameters for screwing into the bone. With this the larger outer diameter is arranged on the side of the conical casing region with the larger outer diameter in order to permit or favor the screwing in of the locking bolt into the bone and marrowbone nail.

For the purpose of a further reduction of the rotating-in moment and for the reduction of the production of wear and swarf the passage hole in a region of the marrowbone nail may be formed of a reduced wall thickness. By way of this additionally the range of the possible angular alignments is increased. For this purpose the thread in the passage hole may have only a few complete windings. Furthermore for this on the region of the passage hole carrying the thread, which previously may be formed crowned, on at least one side of the marrowbone nail there may be connected a region of the passage hole extending spherically or conically outwards. For securing the locking bolt in its angular position this furthermore in the casing region may comprise a shoulder which as a seat surface cooperates with the spherical or conical region of the passage hole likewise forming a seat surface. By way of this, but also by way of the conical formation of the casing region and where appropriate the bone thread a securement of the locking nail is achieved which renders a securement by way of support of a bolt head on the bone surface more or less superfluous. For applying the locking bolt it is in any case advantageous when this has a head with a tool engagement which as a rule however need not project beyond the bone.

According to a further formation of the invention the connection carrier comprises a sensor—e.g. a wire strain gauge ("WSG")—for determining the force being transmitted by the connection carrier between the bone ends, and a sensor for the telemetric transmission of the readings. The sensor and/or transmitters may be integrated into a cavity of the connection carrier. By way of this a monitoring of the loading of the bone and thus a control of the healing process is made possible and corrections of the behavior of the patient are simplified.

Preferably the bone screw, locking bolts and/or connection carrier consist of titanium, wherein for the bone screw, locking bolt and connection carriers or parts of these system components titaniums with varying material properties may be applied.

For the purpose of improving the centering of the bone screw on rotating into the bone on the seat surface of the connection carrier there may be applied a hole gauge of the fixation system with a contour complementary to the seat surface. By way of a drill hole of the hole gauge a hole may be predrilled in the bone. By way of this the central primary position of the seat surface of the bone screw is ensured on rotating the screw into the passage hole into the bone.

BRIEF DESCRIPTION OF THE DRAWINGS

Further details and advantages of the invention result from the subsequent description of preferred embodiment forms. In the drawings there are shown:

FIG. 3 an elongate passage hole in a plan view of part of a connection carrier;

FIG. 4 an elongate passage hole in a part longitudinal section through the connection carrier;

FIG. 5 the same elongate passage hole with an applied bone screw in two displacement positions in a part longitudinal section through a connection carrier and a bone located thereunder;

DETAILED DESCRIPTION OF THE INVENTION

Figure 1:
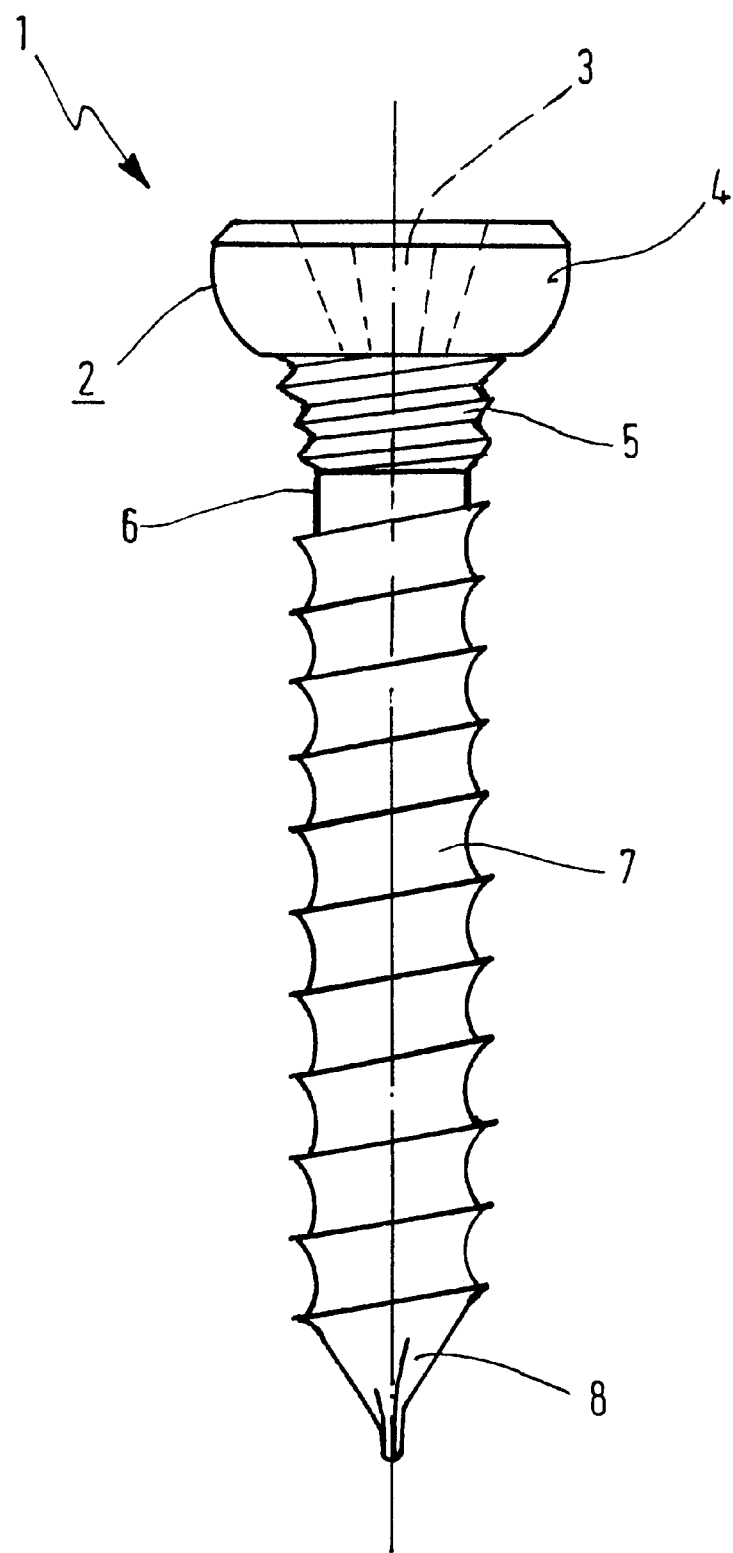
FIG. 1 a bone screw in a front view.

The bone screw 1 according to FIG. 1 has a screw head 2 which at the top has a hexagonal inbus 3, at the bottom a spherical seat surface 4 and therebelow a short preformed thread 5. Thereunder there is connected a screw shank. This carriers a bone thread 7 as well as a screw tip 8, wherein the screw tip 8 may also be shaped as a drill tip so that it is self-drilling for the bone, and the bone thread may be formed as a self-cutting thread.

FIG. 2a to 2i show varying formations of passage holes 9 in connection carriers 10 which are in each case formed as bone plates.

According to FIG. 2a below a conical seat surface 11 roughly centrally in the passage hole 9 there is arranged an annulus-shaped projection (or ridge) in the passage hole 9. Thereunder the passage hole 9 in turn has a conical extension 13.

Figure 2:
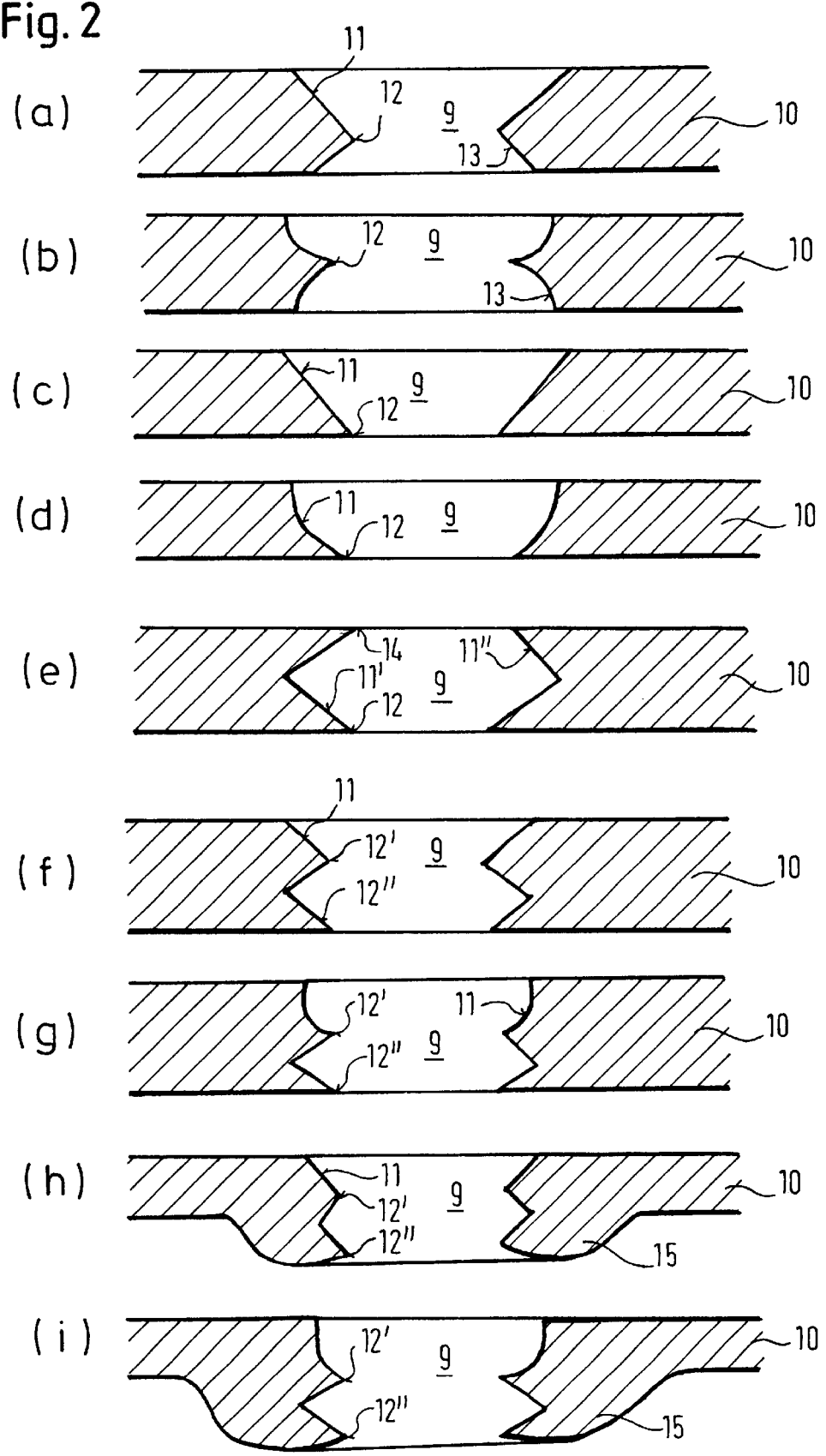
FIGS. 2a to 2i various formed-out passage holes in a part section through a connection carrier.

According to FIG. 2b in the passage hole 9 above there is formed a conical seat surface which blends into projection 12 running circumferentially in an annulus-shaped manner, roughly in the middle of the passage hole 9. Thereunder the passage hole 9 has a spherical extension 13.

FIG. 2c and FIG. 2d show passage holes 9 on whose base there is arranged a projection 12. With this the projection 12 below limits a conical seat surface 11 (FIG. 2c) or a spherical seat surface 11 (FIG. 2d).

According to FIG. 2d the passage hole 9 at the lower end is limited by a projection 12 and at the upper end by a further projection 14. The projection 12 is formed at the lower end of a lower seat surface 11' tapering downwards and the upper projection 14 at the upper end of an upwardly tapering upper seat surface 11". In cross section thus the passage hole 9 in the connection carrier 10 has a "swallowtail" shape.

According to FIG. 2f also below a cone-shaped seat surface there may be present two projections 1', 12" of which one 12" simultaneously represents the end of the seat surface and the further projection 12" is arranged at an axial distance to the first-mentioned projection 12'.

The passage hole 9 according to FIG. 2g is distinguished only in that the seat surface 11 is formed spherically above the two projections 12', 12".

With the embodiment according to FIG. 2h the passage hole 9 in contrast to the embodiment according to FIG. 2f has a bulge-shaped material thickening 15 which is arranged on the lower side of the connection carrier 10. Also with this embodiment below a conical seat surface 11 tapering downwards there is located a projection 12' limiting this and at a distance thereunder a further projection 12".

With the embodiment form according to FIG. 2i in contrast to the embodiment form according to FIG. 2g there is likewise arranged a bulging material thickening around the passage hole 9, which in turn is arranged on the lower side of the connection carrier 10. Also here a spherical seat surface 11 is limited by a projection 12' and at a distance under this there is located a further projection 12".

A bone screw 1 can be rotated in at various angular positions with respect to the axis of the passage holes 9 of the embodiments of a connection carrier 10 according to FIGS. 2a to 2i. With this the preformed thread 5 deforms the projections 12 or 12' and 12" so that a thread connection between the bone screw and the passage hole 9 is formed which is orientated exactly in the screwing-axis. On deforming the material of the projections 12 fills out cavities of the preformed thread 3 or next to the projections so that there results a thread connection in the broadened carrier cross section. Finally the seat surface 4 is seated on the lower side of the ball head on the seat surface 11 of one of the embodiments and by this is supported in the respective screwing-in angle. The screw head 2 then does not project beyond the level of the upper side of the connection carrier 10. Furthermore the bone screw 1 in the achieved end position is secured by a non-positive or friction fitting connection to the respective connection carrier 10 in the region of the projection 12 (or of the projections 12', 12").

FIGS. 3 to 5 show an elongate formation of a passage hole 9' of a bone plate 10' with an angularly stable bone screw— bone plate connection. The passage hole 9' has an elongate extension in the direction of the main axis of the bone plate 10'. It tapers from its one end 9" to its end 9'''. Furthermore it has an upper edge 16 which is inclined from one end 9 to the other end 9'''. Laterally of the upper edge 16 an essentially spherical seat surface 11' is formed, which around the end 9' is completely formed. Here the edge 16 in a region V blends into an easily deformable projection 12 which at the same time limits the passage hole 9' downwards.

According to FIG. 5 a screw inserted into the passage hole 9' slides downwards with the seat surface 4 of its screw head 2 on the edge 16 or the seat surface 11' surrounding this on rotating into a bone fragment 17', by which means there results a displacement of the bone plate 10' with respect to the bone in the direction R and the bone fragment 17' is pressed against a neighboring bone fragment 17". If the screw head 2 is seated on the seat surface 11' and is completely contained in the passage hole 9' the preformed thread 5 by way of deformation of the projection 12 has formed an angularly stable screw connection. In the then reached compression position the bone fragments 17', 17" are held pressed together.

Figure 6:
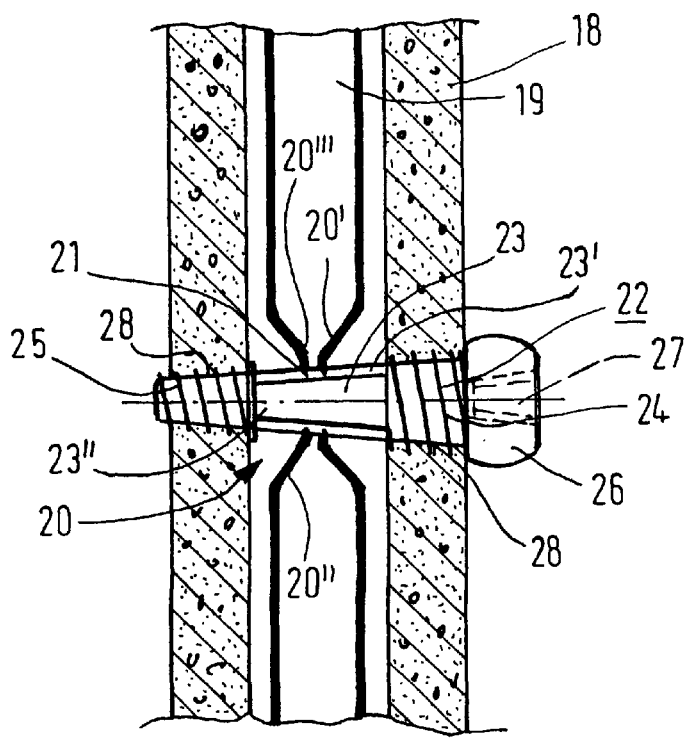
FIG. 6 a marrowbone nail with locking bolts in a tubular bone in a schematic longitudinal section.

According to FIG. 6 into a tubular bone 18 which at a location not shown comprises a fracture there is applied a bonemarrow nail 19. This on both sides of the fracture comprises at least one passage hole 20. The passage hole 20 has on both sides regions 20', 20" which expand spherically outwards and in the middle a region 20''' carrying a thread. The thread-carrying region 20" is convexly curved or rounded towards the middle axis of the passage hole 20. Its thread 21 has roughly three complete circumferential windings. The whole bonemarrow nail 19 may consist of a relatively hard titanium.

Into the passage holes 20 on both sides of the fracture there are applied locking bolts 22. A locking bolt 22 has generally a conical middle section 23 which has an outer conical coating region 23' on an outer conical core region 23". On both sides of the conical middle section 23 the locking bolt comprises threads 24, 25 for screwing into the bone, wherein the thread 24 at the end of the middle section 23 with the larger outer diameter has a larger outer diameter than the thread 25 on the other side. The outer diameter of the threads 24, 25 are in each case at least as large as the bordering outer diameter of the conical middle section 23.

At the other end of the thread 24 the locking bolt 22 has a head 26 in which there is formed a tool engagement in the form of a hexagon socket 27.

The locking bolt 22 is likewise manufactured completely of titanium. With this the core region 22", the bone thread 24, 25 and the head 26 consist of a harder titanium material than the coating region 23'.

If the bonemarrow nail is placed and the fragments of the bone 18 are aligned, with the help of an X-ray apparatus the positions of the passage holes 20 are ascertained and here bore holes 28 are incorporated transversely through the tubular bones 18 into the respective passage hole 20. Thereafter the locking bolts 22 are rotated in, wherein these by way of the threads 24, 25 themselves may cut the threads in the bone 18. Furthermore the thread 21 forms a thread into the coating region 23', wherein the strength of this thread connection with an increasing screw advance on account of the conical shape of the coating region 23' increases. An additional securement may be achieved by a basic conical shape of the treads 24,25 and by a placing of the head 26 of the locking bolt 22 on the outer side of the bone 18. Various angular alignments of the locking bolt 22, which for example may result on account of targeting errors with the incorporation of the bore hole 28 are compensated by the formation of the passage holes 20 and the middle sections 23.

Figure 7:
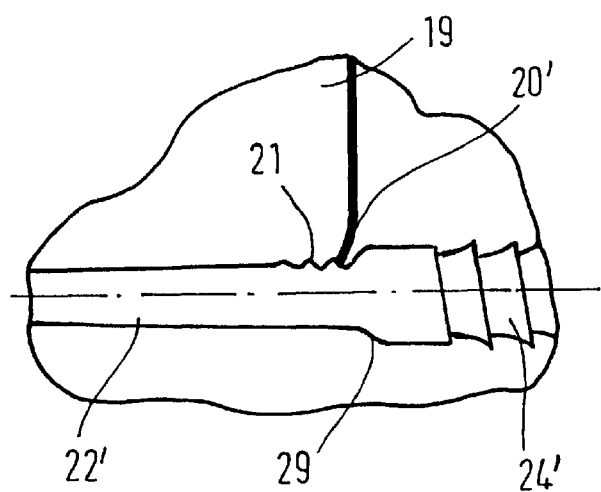
FIG. 7 a locking bolt with a shoulder in the casing region on a seat surface in the passage hole of the marrowbone nail in a part section.

According to FIG. 7 a locking bolt 22' below the thread 24' with the larger diameter may comprise a shoulder 29 which forms a seat surface which rests against the spherical region 20' of the passage hole 20, which likewise forms a seat surface. By way of this a further improvement of the seat of the locking bolt 22' in the bone 18 and the marrow-bone nail 19 is achieved.

What is claimed is:

1. A fixation system for bones comprising:
   a connection carrier with at least one passage hole;
   at least one bone screw inserted into the at least one passage hole;
   the connection carrier including a seat surface and the bone screw including a seat surface, permitting a mutual alignment at various angles for fixing the bone screw at a certain angle to the connection carrier,
   the bone screw further including a preformed thread below the bone screw seat surface, the preformed thread deforming a portion of the passage hole below the seat surface of the connection carrier when the bone screw is screwed in so that a thread connection is formed between the bone screw thread and the connection carrier, the deformation being formed by rotating the bone screw at a certain angle to the connection carrier.

2. A fixation system according to claim 1, wherein the threaded connection is formed by a preformed thread below the bone screw seat surface and at least one at least partly circumferential projection below the connection carrier seat surface, this projection being deformable by way of rotating in the preformed thread.

3. A fixation system according to claim 1, wherein the seat surfaces are spherical or conical.

4. A fixation system according to claim 1, characterised in that the bone screw seat surface is formed on the lower side of the screw head of the bone screw.

5. A fixation system according to claim 1, wherein the thread connection is formed with a section of the screw head below the bone screw seat surface.

6. A fixation system according to claim 5, wherein the thread connection is formed with a preformed thread on the screw head below the bone screw seat surface.

7. A fixation system according to claim 1, wherein the connection carrier seat surface is formed in the passage hole of the connection carrier.

8. A fixation system according to claim 7, wherein above the connection carrier seat surface in the passage hole there is arranged at least yet further, at least partly circumferential projection which is deformable by rotating in the bone screw.

9. A fixation system according to claim 1, wherein the thread connection is formed with a section of the passage hole below the connection carrier seat surface.

10. A fixation system according to claim 9, wherein the threaded connection is formed with a deformable projection in the passage hole below the connection carrier seat surface.

11. A fixation system according to claim 10, wherein at a distance to the deformable projection there is arranged at least one further, at least partly circumferential projection, below the connection carrier seat surface, which is deformable by rotating in the preformed thread.

12. A fixation system according to claim 1, wherein the connection carrier comprises a material thickening around the passage hole.

13. A fixation system according to claim 12, wherein a material thickening is formed on the lower side and/or on the upper side of the connection carrier.

14. A fixation system according to claim 1, wherein the bone screw comprises a shank with a shank thread.

15. A fixation system according to claim 14, wherein the pitch of the preformed thread is slightly smaller than the pitch of the shank thread of the bone screw.

16. A fixation system according to claim 1, wherein the shank thread is a self-cutting thread.

17. A fixation system according to claim 1, wherein the bone screw comprises a drill tip.

18. A fixation system according to claim 1, wherein the screw head comprises a tool engagement.

19. A fixation system according to claim 1, wherein the screw head on the lower side comprises conical furrows for accommodating the deformed material.

20. A fixation system according to claim 1, wherein the passage hole has an elongate shape and the upper edge of the passage hole is inclined from a maximum level at one end to a minimum level at the other end, wherein the width of the passage hole reduces from one end to the other so that a bone screw introduced in the vicinity of the one end, with the screw head is seated on the inclined edge and on screwing with the displacement of the connection carrier, with the head lower side slides on the inclined edge, until on approaching the other end the preformed thread with the deformable projection forms a threaded connection.

21. A fixation system according to claim 1, wherein the axes of the distal passage holes of the connection carrier are inclined to the axes of its proximal passage holes such that the distal and proximal bone screws with their screw heads are closer together that with their feet.

22. A fixation system according to claim 1, wherein the connection carrier is a bone plate, a marrowbone nail or fixator.

23. A fixation system according to claim 1, wherein the preformed thread consists of a harder material than the deformable projection.

24. A fixation system according to claim 1, wherein the bone screw or its casing is of a harder material than the connection carrier or the region to be deformed.

25. A fixation system according to claim 1, wherein the connection carrier comprises a sensor for determining the force transmitted by the connection carrier between the bone ends and a transmitter for the telemetric transfer of the readings.

26. A fixation system according to claim 25, wherein the sensor and/or transmitter are integrated into a cavity of the connection carrier.

27. A fixation system according to claim 1, wherein the bone screw and/or the connection carrier consists of titanium.

28. A fixation system for bones with a marrowbone nail, comprising at least one passage hole, for bridging bone fragments and at least one locking bolt for screwing into the passage hole and into a bone fragment, in order to connect this to the marrowbone nail, wherein the passage hole has an inner thread for forming a thread into the locking bolt and the locking bolt has a threadless and conical casing region which simplifies the forming of a thread by way of the inner thread at various angles, which reduces the wear and release of swarf and ensures the fixing in the formed-in thread, said casing region having a lower hardness than its core region which ensures the transmission of higher forces.

29. A fixation system according to claim 28, wherein the casing region of the locking bolt has a lesser hardness than the bonemarrow nail at least in the region of the inner thread.

30. A fixation system according claim 28, wherein the locking bolt on both sides of the conical casing region carries a thread, wherein the outer diameter of the thread next to the end of the conical casing region with the larger diameter is larger than the outer diameter of the thread next to the end of the casing region with the smaller diameter.

31. A fixation system according to claim 28, wherein the passage hole in a region of the bonemarrow nail is formed of a lesser wall thickness.

32. A fixation system according to claim 28, wherein the inner thread in the passage hole only has a few complete windings.

33. A fixation system according to claim 32, wherein the inner thread in the passage hole has one to four complete circumferential windings.

34. A fixation system according to claim 28, wherein on the thread-carrying region of the passage hole on at least one side of the marrowbone nail there connects a spherically or conically outwardly extending region of the passage hole.

35. A fixation system according to claim 34, wherein the locking bolt comprises a shoulder which is a seat surface for bearing on the conical region, of the passage hole, which forms a seat surface.

36. A fixation system according to claim 28, wherein the locking bolt has a head with a tool engagement.

* * * * *